United States Patent [19]

Sircar

[11] Patent Number: 5,030,775
[45] Date of Patent: Jul. 9, 1991

[54] PROCESS FOR PREPARING MOTOR FUEL GRADE ALCOHOL

[75] Inventor: Shivaji Sircar, Wescosville, Pa.

[73] Assignee: Air Products and Chemicals, Inc., Allentown, Pa.

[21] Appl. No.: 502,093

[22] Filed: Mar. 30, 1990

[51] Int. Cl.⁵ .................... C07C 29/76; C07C 31/08
[52] U.S. Cl. .................................... 568/917; 44/451; 44/453
[58] Field of Search ........................................ 568/917

[56] References Cited

U.S. PATENT DOCUMENTS

| | | | |
|---|---|---|---|
| 2,985,589 | 5/1961 | Broughton et al. | 568/917 |
| 4,273,621 | 6/1981 | Fornoff | 568/917 |
| 4,277,635 | 7/1981 | Oulman et al. | 568/917 |
| 4,319,058 | 3/1982 | Kulprathipanja et al. | 568/917 |
| 4,343,623 | 8/1982 | Kulprathipanja et al. | 568/917 |
| 4,382,001 | 5/1983 | Kulprathipanja et al. | 210/674 |
| 4,407,662 | 10/1983 | Ginder | 55/33 |
| 4,612,405 | 9/1986 | McCaffrey et al. | 568/917 |

OTHER PUBLICATIONS

Garg and Yon (Chemical Engineering Progress, vol. 82, No. 2, pp. 54–60, 2/86).

Primary Examiner—J. E. Evans
Attorney, Agent, or Firm—Keith D. Gourley; James C. Simmons; William F. Marsh

[57] ABSTRACT

A process for preparing motor fuel grade alcohol wherein an ethanol fermentation reactor effluent is distilled to produce an overhead product comprising 10 to about 40 mole percent ethanol and a bottom product comprising the non-alcoholic components. The motor fuel grade alcohol is recovered in high yield from the ethanol/water overhead product mixture in a liquid phase cyclic selective adsorption process which comprises a plurality of adsorption columns operated in cycle in a predetermined time sequence, each adsorption column containing an adsorbent, wherein each respective adsorption column undergoes successive steps of adsorption, desorption and rinsing.

8 Claims, 3 Drawing Sheets

PROCESS FOR PREPARING MOTOR FUEL GRADE ALCOHOL

TECHNICAL FIELD

The present invention relates to a process for preparing motor fuel grade alcohol wherein a carbohydrate fermentation product containing about 3 to 5 mole percent alcohol is separated into its respective components by employing distillation followed by a cyclic concentration swing adsorption process.

BACKGROUND OF THE INVENTION

Diminishing world supplies and decreasing availability of crude oil as well as sporadic regional shortfalls of gasoline for motor fuel have created considerable incentive for the development and use of alternative fuels. Ethanol is gaining wide popularity as such a fuel, particularly when mixed with gasoline to form a mixture known as gasohol. Automobiles can run on gasohol containing up to about 10 volume percent ethanol without requiring engine modifications. Ethanol is also widely used as a chemical solvent and as a raw material in the manufacture of drugs, plastics, lacquers, polishes, perfumes and the like.

Ethanol is derived primarily from the fermentation of mash, usually from corn and/or sugar cane. Natural fermentation is capable of producing an alcohol/water product mixture containing up to about 12 mole percent ethanol. Subsequently, the ethanol is separated from the ethanol/water product mixture via distillation which requires a substantial amount of energy because the mixture forms an azeotrope at a liquid phase composition of about 90.0 mole percent alcohol. Considerable investigation is being conducted to devise a more energy efficient and less capitally intensive process for breaking the ethanol/water azeotrope.

Several processes are known in the art for breaking the ethanol/water azeotrope to form motor fuel grade alcohol containing about 98.0 mole percent alcohol. For example, U.S. Pat. No. 4,319,058 discloses a process for separating ethanol from an ethanol/water feed mixture which comprises contacting the mixture with an adsorbent comprising a shaped replication of particle aggregates comprising carbonaceous pyropolymers containing recurring units of at least carbon and hydrogen atoms at a temperature ranging from about 20° to about 230° C., and a pressure ranging from about atmospheric to about 500 psig, selectively adsorbing substantially all of the ethanol to the substantial exclusion of water and thereafter recovering high purity ethanol by passing a desorbing material over the adsorbent.

U.S. Pat. No. 4,343,623 discloses an adsorptive separation process for separating ethanol from a feedstock mixture comprising ethanol and water. The process comprises contacting the feedstock mixture with an adsorbent comprising esterified silica, selectively adsorbing substantially all of the ethanol to be separated to the substantial exclusion of the water and thereafter recovering high purity ethanol. A desorption step may be used to desorb the adsorbed ethanol from the adsorbent.

U.S. Pat. No. 4,382,001 discloses a process for separating ethanol from a feedstock mixture comprising ethanol and water. The process comprises contacting the feed mixture with an adsorbent comprising activated carbon, selectively adsorbing substantially all of the ethanol to be separated to the substantial exclusion of the water and thereafter recovering high purity ethanol. A desorption step is used to desorb the adsorbed ethanol wherein the desorbent is capable of direct blending into motor fuel.

U.S. Pat. No. 4,407,662 discloses a process for removing sufficient water from an ethanol/water mixture of at least 160 proof to produce ethanol having a proof of 195 or more comprising the steps of heating the ethanol/water mixture until it is a vapor with sufficient super heat to maintain the vapor phase and to prevent substantial capillary adsorption as the mixture passes through a dessicant bed of molecular sieves, passing the super heated ethanol/water mixture through the bed to remove sufficient water to increase the proof of the ethanol to at least 195, passing a portion of the dehydrated ethanol through a second dessicant bed of molecular sieves at less than atmospheric pressure to desorb the water and ethanol on the dessicant from a previous dehydration cycle and reversing the flow through the two beds after the temperature of the first bed increases no more than about 14° C.

An article by Mssrs. Garg and Yon, (Chemical Engineering Progress, Vol. 82 No. 2, pg. 54, February 1986) discloses an adsorptive heat recovery drying system for the energy efficient drying of petrochemical streams containing a substantial amount of water. The process comprises withdrawing a vapor stream containing about 83-90% alcohol from a top tray of a beer column and super heating the stream to prevent condensation. The super heated vapor stream is then dried by selectively adsorbing the water onto a solid adsorbent. The adsorbed water is then desorbed so that the adsorbent can be reused. The regeneration is effected by heating the adsorbent with a hot inert gas such as nitrogen or carbon dioxide in a closed loop recycling system carried out at elevated pressure and temperature.

A need exists in the art for an energy efficient, less capital intensive process for preparing motor fuel grade alcohol, and more particularly, to an energy efficient, cyclic process for recovering motor fuel grade alcohol from the ethanol/water product formed in conventional fermentation reactors.

BRIEF SUMMARY OF THE INVENTION

The present invention provides an energy efficient, cyclic process for preparing motor fuel grade alcohol wherein an ethanol fermentation reactor effluent is distilled to produce an overhead product comprising an ethanol/water mixture and a bottom product comprising non-alcoholic components. A novel cyclic adsorption sequence is employed to separate the ethanol/water overhead distillation product into the motor fuel grade alcohol product and a process stream comprising water which can be recycled for further use in the process. The process for producing motor fuel grade alcohol comprises (a) separating a feedstock comprising a mixture of ethanol and water, and non-alcoholic components into an overhead product comprising the ethanol/water mixture and a bottom product comprising the non-alcoholic components;

(b) introducing the ethanol/water mixture into a plurality of adsorption columns operated in cycle in a predetermined timed sequence, each adsorption column containing an adsorbent wherein the following sequence of operational steps is performed in the order recited in each of the adsorption columns in its turn:
  (1) passing the ethanol/water mixture through an adsorption column containing the solid adsorbent and selectively adsorbing the ethanol while discharging an enriched water stream;
  (2) rinsing the adsorption column in a direction co-current to the flow of the feedstock with ethanol whereby an admixture of residual ethanol and water is displaced from the adsorption column and withdrawing the residual ethanol/water mixture from the adsorption column;
  (3) rinsing the adsorption column with a liquid desorbent whereby the motor fuel grade alcohol is displaced from the adsorbent bed and withdrawing the motor fuel grade alcohol from the adsorption column; and
  (4) rinsing the adsorption column with water in a direction co-current to the flow of the feedstock until the adsorbent is saturated with water and displacing and withdrawing a stream comprising an admixture of the desorbent and water from the adsorption column.

The process according the present invention provides an alternate, energy effluent process for recovering motor fuel grade alcohol from the alcohol/water mixture formed in conventional synthetic fermentation processes.

DETAILED DESCRIPTION OF THE INVENTION

Figure 1:
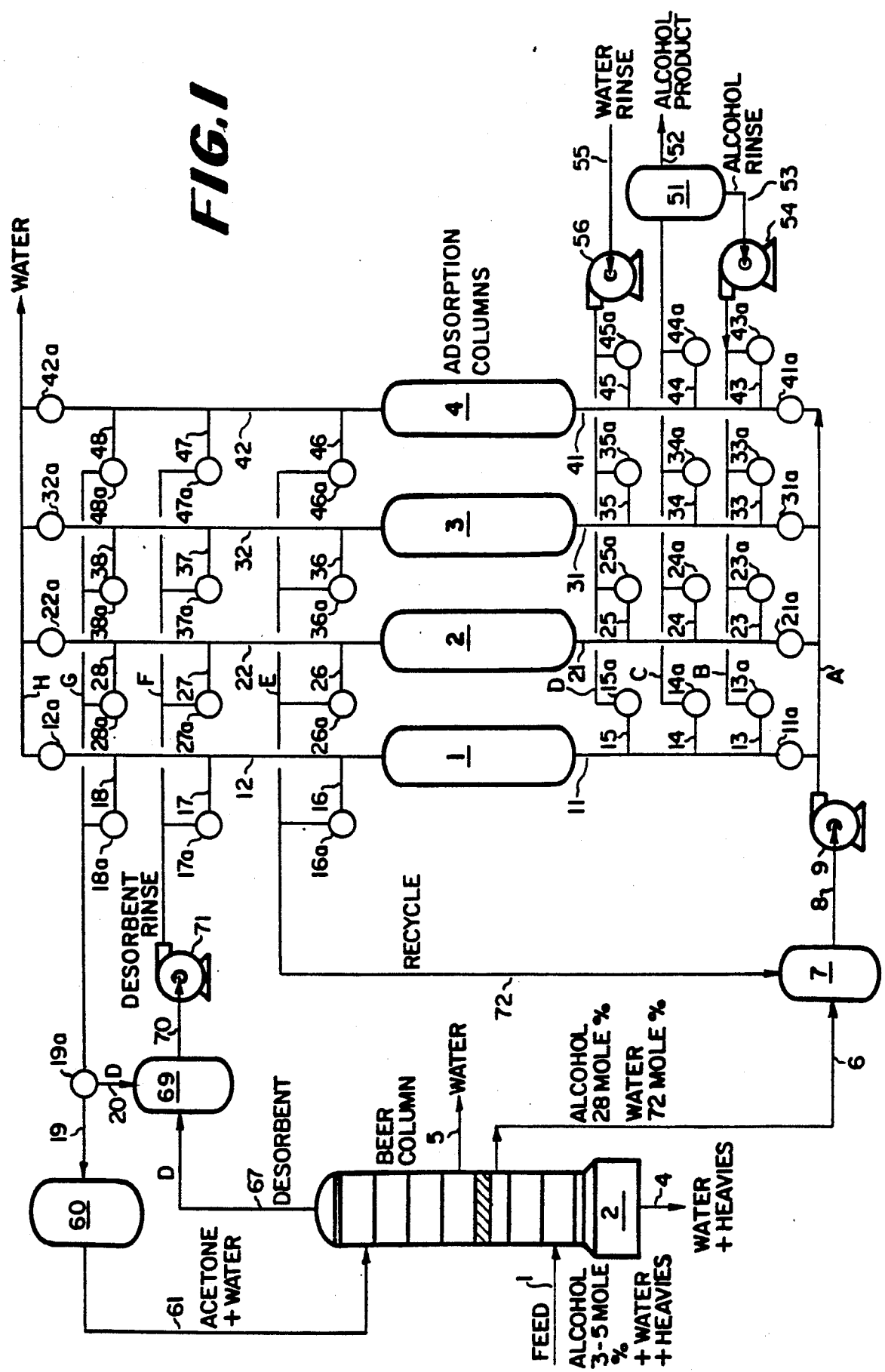
FIG. 1 is a process flow diagram of an embodiment according to the present invention.

The present invention provides an energy efficient, cyclic process for effectively breaking the alcohol/water azeotrope encountered during the production of motor fuel grade alcohol. The term, motor fuel grade alcohol (MFGA) as used in the Specification and Claims, refers to ethanol containing from about 0.5 to about 3.0 mole percent water. Considerable capital costs and energy are required to break the azeotropic alcohol-water mixture into its respective components. The instant process overcomes such shortcomings by employing a novel sequence of steps wherein the effluent from a conventional alcohol fermentation reactor is distilled in a conventional beer column to produce an enriched ethanol stream containing only from 10 to about 40 mole percent ethanol instead of the conventional over-head product of an azeotropic alcohol water mixture containing about 90.0 mole % alcohol. The enriched ethanol stream is then introduced into a unique concentration swing adsorption process sequence wherein motor fuel grade alcohol (MFGA) is recovered from the feed mixture. The cyclic adsorption sequence represents an advance over other continuous, cyclic adsorption processes known in the art by offering an alcohol product of desired purity and very high alcohol recovery of 97-99.5%.

The cyclic adsorption sequence disclosed herein is referred to as a concentration swing adsorption process because the adsorption and desorption steps are governed by changes in concentration of the liquid adsorbates inside the adsorption column containing the adsorbent which selectively adsorbs the alcohol from water.

The process according to the present invention comprises:
  (a) separating a feedstock comprising a mixture of ethanol and water and non-alcoholic components into an overhead product comprising an ethanol/water mixture and a bottom product comprising the non-alcoholic components;
  (b) introducing the ethanol/water mixture into a plurality of adsorption columns operated in cycle in a predetermined timed sequence, each adsorption column containing an adsorbent wherein the following sequence of operational steps is performed in the order recited in each of the adsorption columns in its turn:
    (1) passing the ethanol/water mixture through an adsorption column containing the solid adsorbent and selectively adsorbing the ethanol while discharging an enriched water stream;
    (2) rinsing the adsorption column in a direction co-current to the flow of the feedstock with ethanol whereby an admixture of residual ethanol and water is displaced from the adsorption column and withdrawing the residual ethanol/water mixture from the adsorption column;
    (3) rinsing the adsorption column with a liquid desorbent whereby the motor fuel grade alcohol is displaced from the adsorbent bed and withdrawing the motor fuel grade alcohol from the adsorption column; and
    (4) rinsing the adsorption column with water in a direction co-current to the flow of the feedstock mixture until the adsorbent is saturated with water and displacing and withdrawing a stream comprising an admixture of the desorbent and water from the adsorption column.

The invention will be described in greater detail with reference to FIG. 1 which illustrates a schematic diagram of a cycle for producing motor fuel grade alcohol from a feedstock comprising an ethanol/water mixture and non-alcoholic components. The schematic consists of distillation column 2, four parallel adsorption columns 1 through 4; numerous control valves; liquid manifolds A through H and liquid pumps 9, 54, 56 and 71.

Feedstock containing 3 to about 5 mole percent alcohol in water, as obtained from the fermentation of a carbohydrate source such as corn or sugar cane, is fed through line 1 into beer column 2 to produce an overhead product comprising an azeotropic ethanol/water mixture containing 10 to about 40 mole percent ethanol, and a bottom product comprising non-alcoholic components including heavy impurities such as aldehydes and ketones and solid matter such as husks and the like. Typically, only a part (approximately one-third to one-half of the trays) of the conventional beer column is used to concentrate the raw alcohol feed. The ethanol/water distillation effluent, containing 10 to about 40 mole percent ethanol, is then fed to one of adsorption columns 1 through 4 such that the ethanol/water azeotrope can be broken in order to recover the motor fuel grade alcohol. More particularly, the ethanol/water mixture exits beer column 2 via line 6 and flows into storage tank 7 and is introduced into line 8, via pump 9, through Manifold A and into the desired adsorption column.

Manifold A is in flow communication with branch inlet lines 11, 21, 31 and 41 which are connected to the inlet ends of adsorption columns 1, 2, 3 and 4. Lines 11, 21, 31 and 41 are equipped with valves 11a, 21a, 31a and 41a, respectively. Opening of the appropriate valve permits flow of the feedstock into the selected adsorption column being initially placed on stream. Thus, by opening valve 11a, while valves 21a, 31a and 41a are closed, feedstock is caused to flow from manifold A through line 11 and into adsorption column 1.

Adsorption columns 1, 2, 3 and 4 are fitted at their respective outlet ends with lines 12, 22, 32 and 42, respectively, each further equipped with control valves 12a, 22a, 32a and 42a, respectively. Lines 12, 22, 32 and 42 are operatively connected to manifold H. By opening the appropriate valve 12a, 22a, 32a or 42a, water is caused to flow from the corresponding adsorption column through line 12, 22, 32 or 42 and into manifold H to be collected as product.

Adsorption columns 1, 2, 3 and 4 are operatively connected to lines 13, 23, 33 and 43, each being further provided with control valves 13a, 23a, 33a and 43a, respectively, such lines being in flow communication with manifold B. Manifold B is in flow communication with storage tank 51 wherein ethanol is stored as product. Ethanol can flow through line 53 and through pump 54 into manifold B. Each adsorption column is placed in flow communication with discharge manifold C via lines 14, 24, 34 and 44, each of which is equipped with control valves 14a, 24a, 34a and 44a. By opening the appropriate valve 14a, 24a, 34a and 44a, liquid from the inlet end of the appropriate column passes through line 14, 24, 34, or 44 and into manifold C for storage in storage tank 51 prior to collection as product via line 52 or use as a column rinsing liquid through manifold B.

Adsorption columns 1, 2, 3 and 4 are placed in flow communication with manifold D via lines 15, 25, 35 and 45 which are each fitted with control valves 15a, 25a, 35a and 45a. By opening the appropriate control valve, water is caused to pass through line 55, liquid pump 56 into manifold D and line 15, 25, 35, or 45 into the inlet end of the appropriate adsorption column.

The discharge ends of columns 1, 2, 3 and 4 are operatively connected to manifold E via lines 16, 26, 36 and 46, which are fitted with control valves 16a, 26a, 36a and 46a, respectively. By opening the appropriate valve 16a, 26a, 36a or 46a, liquid from a particular adsorption column enters lines 12, 22, 32 or 42 flowing into lines 16, 26, 36, or 46 and into manifold E. Manifold E is operatively connected to storage container 7 via line 72.

Adsorption columns 1, 2, 3 and 4 are operatively connected to manifold F via lines 17, 27, 37, and 47 which are connected to lines 12, 22, 32 and 42, respectively. Lines 17, 27, 37 and 47 are equipped with control valves 17a, 27a, 37a and 47a, respectively. By opening the appropriate control valve 17a, 27a, 37 or 47a, desorbent liquid stored in storage tank 69 is caused to be pumped through line 70, manifold F and into the appropriate adsorption column via lines 17, 27, 37 and 47, respectively. Liquid pump 71 provides the pressure necessary to effect such transfer. Manifold F is operatively connected to beer column 2 and manifold G. For example, overhead distillation product from beer column 2 is passed through line 67 and into storage tank 69. Liquid from storage tank 69 is passed through line 70, through pump 71 and into manifold F. Storage tank 69 is also connected to manifold G via line 20.

Adsorption columns 1 through 4 are operatively connected to manifold G by lines 18, 28, 38 and 48 which are in flow communication with lines 12, 22, 32 and 42, respectively. By opening control valve 18a, 28a, 38a or 48a, liquid from the respective adsorption column is caused to pass through line 12, 22, 32 or 42, through lines 18, 28, 38 or 48, respectively, and into manifold G. Manifold G is fitted with control valve 19a wherein liquid can be directed to storage tank 60 via line 19 and into beer column 2 via line 61; or to storage tank 69 via line 20.

Operation of the embodiment represented in FIG. 1 will now be explained in connection with an arbitrarily chosen cycle having four timed separation periods of 30 minutes per period as set forth in Table 1. Although not limited thereto, the process as illustrated in FIG. 1 requires 4 adsorption columns for continuous operation. However, other arrangements using fewer adsorption columns may be employed if interrupted or discontinuous operation (using idling) of pumps is acceptable. Other arrangements may also be employed (e.g., employing more than four adsorption columns) by appropriate sequencing of the individual steps of the process cycle. Similarly, the total cycle time of 120 minutes for the adsorption process is an example. Total cycle times of 4 to 480 minutes can be employed depending on the plant size.

TABLE 1

| Time | Column 1 | Column 2 | Column 3 | Column 4 |
|------|----------|----------|----------|----------|
| 0–t1 | Adsorption | B-Rinse | D-Rinse | A-Rinse |
| t1–t2 | A-Rinse | Adsorption | B-Rinse | D-Rinse |
| t2–t3 | D-Rinse | A-Rinse | Adsorption | B-Rinse |
| t3–t4 | B-Rinse | D-Rinse | A-Rinse | Adsorption |

A-Rinse = Alcohol Rinse
D-Rinse = Desorbent Rinse
B-Rinse = Water Rinse

Each of the four respective adsorption columns 1 through 4 undergoes one period of the adsorption step, one period of the alcohol rinse step, one period of the desorbent-rinse step and one period of the water rinse step. As illustrated in Table 1, the steps undertaken at startup in each of the adsorption columns 1 through 4 are staggered to enable at least one of the four adsorption columns to undergo the adsorption step at all times during the process cycle. The operation of the invention described in FIG. 1 involves principally the following sequence of steps:

(a). Adsorption—a stream of the ethanol/water mixture is passed through an adsorption column containing an adsorbent preferentially selective toward retention of ethanol wherein an effluent stream enriched in water is withdrawn from the adsorption column. Ethanol is selectively adsorbed onto the adsorbent and a mass transfer zone (MTZ) is formed inside the adsorbent which moves toward the outlet or discharge end of the column as more feedstock liquid is passed. The adsorbent at the leading edge of the mass transfer zone is saturated with a water-rich liquid while the trailing edge of the MTZ is saturated with a mixture of water and ethanol. The adsorption step is continued until the adsorbent is essentially saturated with the feed mixture. The enriched water liquid is discharged from the adsorption column.

(b). Alcohol-Rinse—the adsorption column is rinsed with a liquid stream which is very rich in ethanol. This rinse step is carried out in a direction co-current to the direction of the feedstock flow. The adsorption column effluent during this step has a feed-like composition (ethanol and water) which is recycled as additional feedstock. The alcohol-rinse step is continued until the adsorption column is essentially saturated with ethanol.

(c). Desorbent-Rinse—the adsorption column is rinsed with a desorbent liquid. The effluent from the adsorption column is a liquid rich in ethanol which is partly withdrawn as MFGA product and partly stored for use as ethanol-rich rinse liquid in step (b). The effluent in the latter part of this step may contain an admixture of desorbent and ethanol which may optionally require an additional separation by distillation to produce an ethanol product stream and a desorbent product stream to be used again in step (C).

(d). Water-Rinse—at the end of step (c), the adsorption column is rinsed with an enriched water stream. The effluent from the column is initially very rich in desorbent which is stored for use as desorbent-rinse fluid in step (c). The remaining effluent is an admixture of desorbent and water which is separated by distillation to produce a desorbent rich product stream and a water product stream. The desorbent stream is recycled to supply the desorbent-rinse liquid in step (c). The adsorption column is essentially saturated with water at the end of this step and a new process cycle begins with step (a).

The valve positions during the above-mentioned operating cycle are set forth in Table 2. The designation 0 indicates that the valve is open while a C represents a closed valve. The operative sequence of steps occurring in adsorption column 1 during a complete adsorption cycle will now be described in exhaustive detail so that operation of a continuous process will be fully understood. The identical sequence of steps according to Table 1 occurs in staggered sequence in adsorption columns 2, 3 and 4.

TABLE 2

| VALVE OPERATION SCHEDULE | | | | |
|---|---|---|---|---|
| Valve | 0–t1 | t1–t2 | t2–t3 | t3–t4 |
| 11a | O | C | C | C |
| 12a | O | C | C | C |
| 13a | C | O | C | C |
| 14a | C | C | O | C |
| 15a | C | C | C | O |
| 16a | C | O | C | C |
| 17a | C | C | O | C |
| 18a | C | C | C | O |
| 19a | C | C | C | C |
| 21a | C | O | C | C |
| 22a | C | C | O | C |
| 23a | C | C | O | C |
| 24a | C | C | C | O |
| 25a | O | C | C | C |
| 26a | C | C | O | C |
| 27a | C | C | C | O |
| 28a | O | C | C | C |
| 31a | C | C | O | C |
| 32a | C | C | O | C |
| 33a | C | C | C | O |
| 34a | O | C | C | C |
| 35a | C | O | C | C |
| 36a | C | C | C | O |
| 37a | O | C | C | C |
| 38a | C | O | C | C |
| 41a | C | C | C | O |
| 42a | C | C | C | O |
| 43a | O | C | C | C |
| 44a | C | O | C | C |
| 45a | C | C | O | C |
| 46a | O | C | C | C |
| 47a | C | O | C | C |

TABLE 2-continued

| VALVE OPERATION SCHEDULE | | | | |
|---|---|---|---|---|
| Valve | 0–t1 | t1–t2 | t2–t3 | t3–t4 |
| 48a | C | C | O | C |

Again, referring to the embodiment disclosed in FIG. 1 and the sequence periods and valve positions designated in Tables 1 and 2, adsorption column 1 undergoes one sequence period of the adsorption step. Feedstock comprising an admixture of ethanol and water, stored in storage tank 7, is introduced into adsorption column 1 by opening valves 11a and 12a and closing valves 13a, 14a, 15a, 16a, 17a and 18a thereby allowing feedstock to flow through line 8, manifold A, line 11 and into adsorption column 1 which contains an adsorbent preferentially selective toward adsorption of ethanol.

The adsorption step is continued until column 1 is essentially saturated with the feed mixture. The flow of liquid is assisted by pump 9. Ethanol is selectively adsorbed onto the adsorbent and a mass transfer zone (MTZ) is formed inside the adsorbent which moves toward the discharge end of adsorption column 1 as more feedstock is passed. The adsorption step is completed when the MTZ reaches the effluent end of the column or somewhat short of it by a predesigned set point. The less selectively adsorbed water component exits the discharge end of column 1 via line 12 and flows into manifold H for discharge or use in the water rinse step.

At the end of the adsorption step, Column 1 is rinsed with a liquid stream rich in ethanol. More particularly, valves 13a and 16a are opened enabling a rinse stream rich in ethanol, stored in storage tank 51, to be pumped via pump 54 through line 53, manifold (B) and lines 13 and 11 into column 1 in a direction co-current to the feedstock. The adsorption column effluent during this step has a feed-like composition (ethanol and water) which is passed through line 16, valve 16a, manifold E and line 72 to be mixed with fresh feedstock in storage tank 7. This step is continued until adsorption column 1 is essentially saturated with ethanol.

The next step in the cycle involves rinsing adsorption column 1 with a desorbent. Control valves 17a and 14a are opened and desorbent liquid is pumped via pump 71 through line 70, manifold F and lines 17 and 12 into column 1 in a direction counter-current to the flow of the feedstock. The effluent is an enriched ethanol stream which is withdrawn from the inlet end of column 1 passing through lines 11 and 14 and manifold C to be collected as motor fuel grade alcohol product or stored in storage vessel 51. This step is continued until adsorption column 1 is essentially saturated with the desorbent. During this step, the latter portion of the effluent from the column 1 may contain an admixture of ethanol and desorbent which can be separated by distillation to produce an ethanol product and a desorbent product. The ethanol stream can be sent to storage tank 51 and the desorbent stream can be sent to storage tank 69. If this option is practiced, a distillation column will be required to process a part of the column effluent in manifold C (not shown in FIG. 1). Furthermore, it should be understood that the flow of the desorbent stream into the column in a direction countercurrent to feed flow is optional. It may be necessary or desirable to direct the flow of the D-rich stream into the column in a direction co-current to feed flow.

Following the desorbent-rinse step, column 1 undergoes a water-rinse step wherein an enriched water stream is passed through column 1 in a direction co-current to the direction of the feedstock. Valves 15a and 18a are opened and pump 56 is used to flow the enriched water stream through line 55, manifold D, line 15 and line 11 into column 1 until the column is essentially saturated with water.

The column effluent during the water-rinse step is initially very rich in desorbent and valves 15a, 18a and 19a are opened allowing the effluent to pass through line 12, manifold G and line 20 to be stored as desorbent-product in storage vessel 69. Thereafter, valve 19a is readjusted to allow the remaining effluent mixture of water and desorbent liquid to pass through line 19 into storage vessel 60 which provides feed for beer column 2 via line 61. The distillation of the water/desorbent admixture produces an enriched water stream which is collected as product and/or used in the water-rinse step line 55. The desorbent can then be recycled for use in the desorbent-rinse step through storage tank 69. Column 1 is now essentially saturated with water at the end of this step and the column is prepared to begin another process cycle. Again, it should be understood that the flow of water-rich fluid into the column during this step can be counter or co-current to the direction of feed flow.

The process proceeds according to the above-mentioned steps enumerated in Table 1. While the sequence periods are depicted as being of equal length, this is neither required or necessary. The times will be set by allowable maximum liquid flow rates, valve and line sizes and the properties of the adsorbent used. Alternate routines may be employed for establishing the duration of each of the cycle steps. For example, the end of a particular step may be determined by other techniques known in the art such as by analysis of the composition of the adsorption column effluent.

The composition of the water/desorbent liquid admixture produced in the latter part of the water-rinse step of the process and which is separated by distillation varies with time during this step. Initially the composition comprises essentially desorbent and then the composition changes to essentially pure water. This mixture of components can be collected in storage tank 60 for mixing and then fed to a particular tray in beer column 2 as a fluid stream of constant composition or the stream can be split into several (two or three) mixed streams of varying composition and then fed at different tray levels in the beer column. The later approach is preferred. The same phenomenon and operation is valid if the latter part of the effluent of step (c), the desorbent rinse step, is separated by distillation to produce a D-rich and an A-rich stream.

The conventional beer column 2 provides a dual role according to the present invention. The bottom section of the column (⅓-½ trays) is used to distill the fermentor effluent in order to produce an overhead stream containing 10-40 mole percent alcohol and water which is fed to the adsorption system. The top section of the beer column is used to distill the desorbent water mixture effluent produced in the latter half of step (d) of the adsorption cycle in order to produce a desorbent and a water stream. The two sections of the column are heat integrated (shaded area in FIG. 1) so that energy is conserved and part of the energy from the overhead product of the bottom section is used in the reboiler for the top section.

Figure 2:
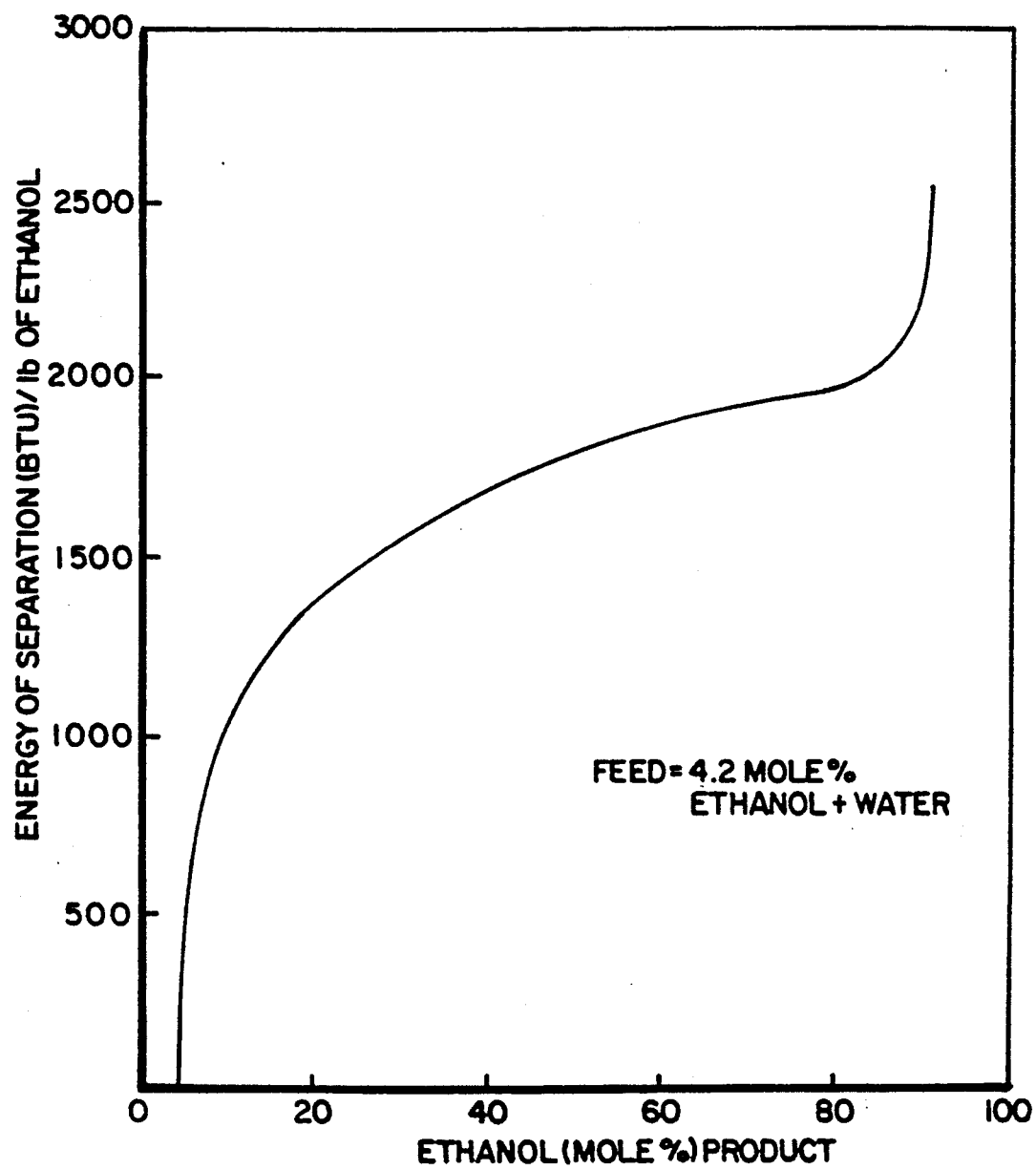
FIG. 2 is a graphic representation of distillation energy (BTU/lb of ethanol) required to produce an ethanol product having a defined purity from a feed mixture containing about 4.0 mole percent alcohol and water.

FIG. 2 presents a graphic representation of the energy (BTU/lb of ethanol) needed to produce an ethanol product of defined purity (mole percent) from a feed mixture containing 4.2 mole percent ethanol and water by conventional distillation. The figure illustrates that the energy required to separate the mixture increases drastically when the product purity is greater than 20 mole percent ethanol and, in particular, when product purity is greater than 85 mole percent ethanol. The process according to the present invention substantially reduces the power requirement necessitated by prior art processes by concentrating the raw ethanol feed from about 4 mole percent to about 20 to 30 mole percent by distillation and then from 30 mole percent to about 99 mole percent by the cyclic concentration swing adsorption sequence.

The process according to this invention is preferably run utilizing adsorbents having a relatively small particle diameter of about 0.2 to about 0.8 mm although a broad range of particle sizes can be employed. This preferred particle size will shorten the distance of diffusion of the adsorbate molecules and will enhance the rate of adsorption. On the other hand, smaller particles will increase the pressure drop within the column during all steps of the process cycle. This pressure drop is overcome by compressing the liquid streams entering the adsorbent within each adsorption column to a pressure of about 10 to 150 psig. Since liquids are incompressible fluids, such compression will not significantly add to the energy requirements of the process. A broad range of adsorbents are known in the art for selectively adsorbing ethanol from an ethanol/water mixture.

Desorption conditions for the process generally include the same range of temperatures and pressures as described for the adsorption step. The desorbent liquid relied upon must be carefully selected to satisfy several criteria. For example, the desorbent must displace the adsorbed ethanol from the adsorbent with reasonable mass flow rates without itself being so strongly absorbed as to unduly prevent the ethanol from displacing the adsorbent in a following adsorption cycle. Moreover, the desorbent material must be compatible with the particular adsorbent and the particular feed mixture. It must not form an azeotrope with ethanol, water or the feed mixture.

Preferred desorbent material for use in the process may be one or a mixture of the common ingredients of gasoline, particularly aromatic and other high octane liquid hydrocarbons. In a preferred embodiment, the desorbent is acetone.

Figure 3:
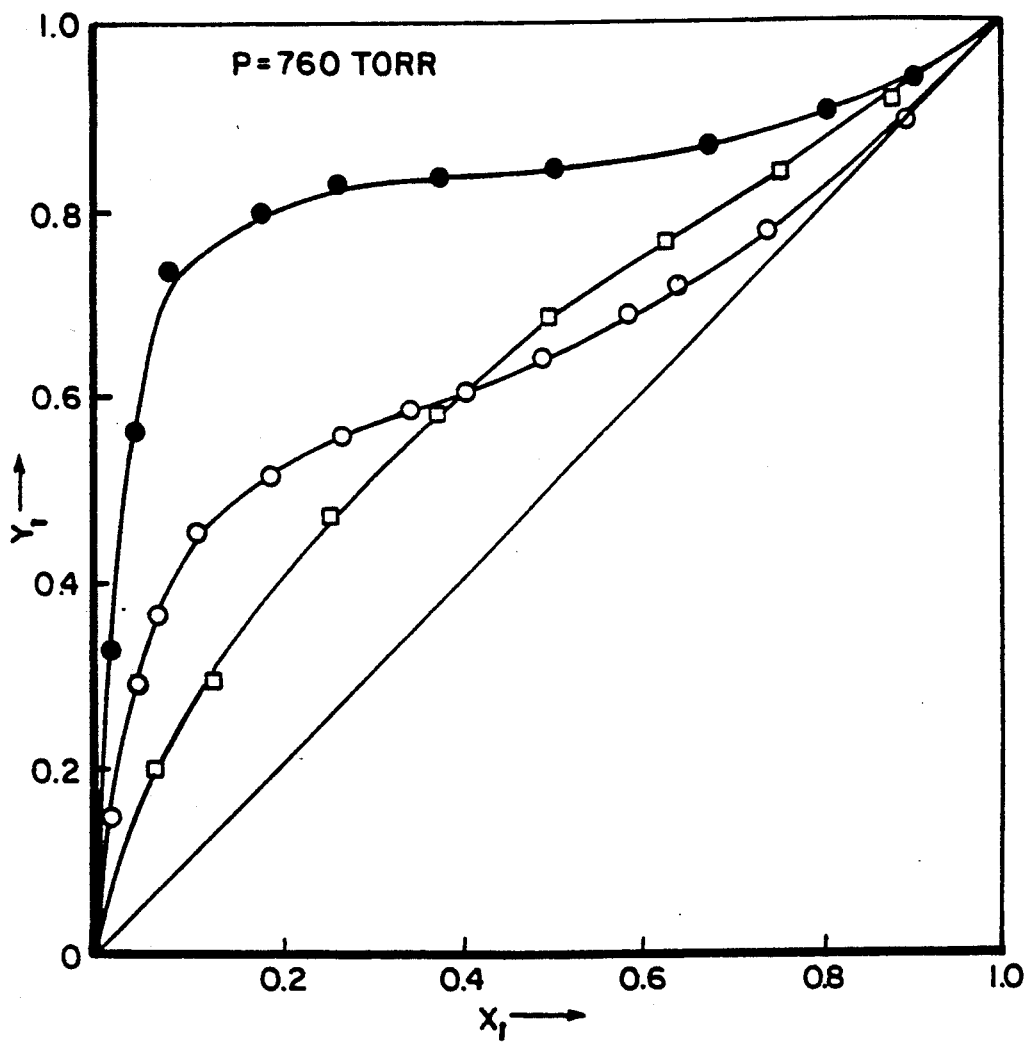
FIG. 3 is a vapor-liquid equilibrium diagram for ethanol-water, acetone-water and acetone-ethanol mixtures at a total pressure of 1.0 atmosphere.

FIG. 3 shows the vapor-liquid equilibrium diagrams for ethanol-water, acetone-water and acetone-ethanol mixtures at a total pressure of 1.0 atmosphere. FIG. 2 plots liquid phase mole fraction of component 1 ($x_1$) in equilibrium with the vapor phase mole fraction of the same component ($y_1$). The graph demonstrates that the ethanol-water mixture forms an azeotrope at $x_1=0.9$ while the acetone-water and ethanol-acetone mixtures exhibit large differences between $x_1$ and $y_1$ in the entire composition range making possible an efficient separation by distillation.

The following Example is provided to further illustrate an embodiment of this invention and is not intended to restrict the scope of the claimed invention.

EXAMPLE 1

Operation of a Four-Bed Cyclic Adsorption Motor Fuel Grade Alcohol Unit

This example illustrates the design and operation of a simulated plant according to the FIG. 1. The plant consists of four 8' diameter by 13.0' long adsorption columns packed collectively with 17,500 lbs. of 0.5 mm diameter activated carbon particles, which selectively adsorbs alcohol from water. A conventional fermentation reactor known in the art is utilized wherein the reactor is designed to produce 3–5 mole percent ethanol at a production rate of 14 MM gals/year contained alcohol.

The feed is introduced into a beer column to produce an enriched alcohol stream having 28 mole percent ethanol. The enriched ethanol stream is introduced into the concentration swing adsorption system at a temperature ranging from 90°–100° F. and 30 psig. The four bed cyclic adsorption unit is operated utilizing a 180 minute cycle according to the sequence enumerated in Table 1.

Table 3 presents a description of various process streams and apparatus according to FIG. 1. Results from a simulation demonstrate that the process according to the present invention is substantially more energy efficient then prior art processes. For example, first pass energy calculations demonstrate that the present process requires approximately 11,000 BTU/gal of MFGA while the process according to Mssrs. Garg and Yon, described in the Background of the Invention requires approximately 14,000 BTU/gal. Those skilled in the art will appreciate the instant process can also be used, without substantial adaptation, to separate and recover other alcohols from a feedstock comprising an azeotropic or close boiling mixture of other alcohols and water.

TABLE 3

| Adsorption Cycle and Process Stream/Equipment Description | | |
|---|---|---|
| Cycle Time | | |
| Adsorption | 30 Minutes | |
| Ethanol Rinse: | 30 Minutes | |
| Desorbent Rinse: | 30 Minutes | |
| Water Rinse: | 30 Minutes | |
| Pumps | FIG. Number | Output (gpm) |
| Feed | 9 | 134 |
| Alcohol Rinse | 54 | 69 |
| Acetone Rinse | 71 | 94 |
| Water Rinse | 56 | 225 |
| Stream No. | Stream Description | Gal/Min |
| 6 | Feed to Adsorption Column | 55 |
| 53 | Alcohol Rinse | 69 |
| 55 | Water Rinse | 225 |
| Manifold E | Recycle | 79 |
| Manifold H | Water Effluent | 115 |
| 61 | Recycle to Distillation | 201 |

TABLE 3-continued

| Adsorption Cycle and Process Stream/Equipment Description | | |
|---|---|---|
| 70 | Desorbent Rinse | 28.1 |

Having thus described the present invention, what is now deemed appropriate for Letters Patent is set forth in the following appended claims.

We claim:

1. A process for producing motor fuel grade alcohol which comprises
   (a) separating a feedstock comprising non-alcoholic components and a mixture of ethanol and water into an overhead product comprising an ethanol/water mixture and a bottom product comprising the non-alcoholic components;
   (b) introducing the ethanol/water mixture into a first adsorption column containing an adsorbent wherein the following sequence of operational steps is performed:
      (1) passing the ethanol/water mixture through the first adsorption column containing the adsorbent and selectively adsorbing the ethanol while discharging an enriched water stream;
      (2) rinsing the first adsorption column with ethanol in a direction co-current to the flow of the feedstock whereby a mixture of residual ethanol and water is displaced from the first adsorption column and withdrawing the residual ethanol/water mixture from the adsorption column;
      (3) rinsing the first adsorption column with a liquid desorbent whereby the motor fuel grade alcohol is displaced from the adsorbent and withdrawing the motor fuel grade alcohol from the adsorption column; and
      (4) rinsing the first adsorption column with water in a direction co-current to the flow of the feedstock until the adsorbent is saturated with water and displacing and withdrawing a stream comprising an admixture of the desorbent and water.

2. The process according to claim 1 wherein the first adsorption column containing the adsorbent is one of a plurality of parallel adsorption columns wherein each of the adsorption columns undergoes in turn steps (b)(1) through (b)(4).

3. The process according to claim 2 wherein the residual ethanol/water mixture according to step (b:2) is recycled with the feedstock.

4. The process according to claim 2 wherein the liquid desorbent is acetone.

5. The process according to claim 2 wherein the adsorbent is activated carbon.

6. The process according to claim 2 wherein the ethanol/water mixture is introduced into the plurality of adsorption columns at a pressure ranging from 10 to about 150 psig.

7. The process according to claim 2 wherein the admixture of water and adsorbent produced in step (b)(4) is separated by a distillation process which is heat integrated with the distillation process of step (a).

8. The process according to claim 2 wherein the separating in step (a) is effected using a beer column.

* * * * *

UNITED STATES PATENT AND TRADEMARK OFFICE
CERTIFICATE OF CORRECTION

PATENT NO. : 5,030,775
DATED     : July 9, 1991
INVENTOR(S) : Sircar

It is certified that error appears in the above-identified patent and that said Letters Patent is hereby corrected as shown below:

Column 5, line 59, delete "37" and insert -- 37a --.

Column 12, line 58, delete "adsorbent" and insert -- desorbent --.

Signed and Sealed this

Ninth Day of February, 1993

Attest:

STEPHEN G. KUNIN

*Attesting Officer*   Acting Commissioner of Patents and Trademarks